United States Patent [19]

Landau et al.

[11] Patent Number: 4,581,021
[45] Date of Patent: Apr. 8, 1986

[54] SQUEEZE-ACTUATED SYRINGE

[75] Inventors: Boris Landau, Huntington Beach; Marius Saines, Los Angeles, both of Calif.

[73] Assignee: Ergomed, Huntington Beach, Calif.

[21] Appl. No.: 695,457

[22] Filed: Jan. 28, 1985

[51] Int. Cl.⁴ .............................................. A61M 5/18
[52] U.S. Cl. .................... 604/212; 604/214; 604/187; 222/103; 222/96
[58] Field of Search ............... 604/132, 133, 187, 212, 604/214, 200, 134, 96, 181, 93, 223; 222/96, 103, 95, 97, 153

[56] References Cited

U.S. PATENT DOCUMENTS

| | | |
|---|---|---|
| 798,093 | 8/1905 | Dean . |
| 1,222,814 | 4/1917 | Stotz .................................... 604/214 |
| 1,880,354 | 10/1932 | Mueller ............................... 604/134 |
| 2,618,263 | 3/1951 | Lakso et al. . |
| 2,781,951 | 2/1957 | Hanford .............................. 604/214 |
| 3,099,264 | 7/1963 | Hubbard . |
| 3,114,369 | 12/1963 | Hall . |
| 3,332,579 | 7/1967 | Peters ..................................... 222/96 |
| 4,013,073 | 3/1977 | Cunningham . |
| 4,432,768 | 2/1984 | Brown et al. ....................... 604/200 |
| 4,475,906 | 10/1984 | Holzner ............................... 604/212 |

Primary Examiner—C. Fred Rosenbaum
Assistant Examiner—Karen L. Kaechele
Attorney, Agent, or Firm—Klein & Szekeres

[57] ABSTRACT

A syringe for use with collapsible ampoules pre-filled with a liquid medicament includes a body that forms an open receptacle for the ampoule and a handle attached by a hinge to one end of the body so as to be in opposed relationship with the ampoule. The handle carries a compression pad on its underside, so that the handle can be squeezed toward the body to compress the ampoule. The body has a fitting at its proximal end for the attachment of a double-ended disposable needle. When the needle is attached to the fitting, the distal end of the needle passes through the fitting and punctures the ampoule, allowing the contents of the ampoule to flow into the needle as the ampoule is compressed. In one embodiment, the handle is hinged to the proximal end of the body; in a second embodiment, it is hinged to the distal end. In both embodiments, the pad is maintained in substantially parallel alignment with the longitudinal axis of the body. A lever is advantageously provided on the body which can be selectively moved into engagement with the handle to lock the handle into a preselected position with respect to the body.

26 Claims, 15 Drawing Figures

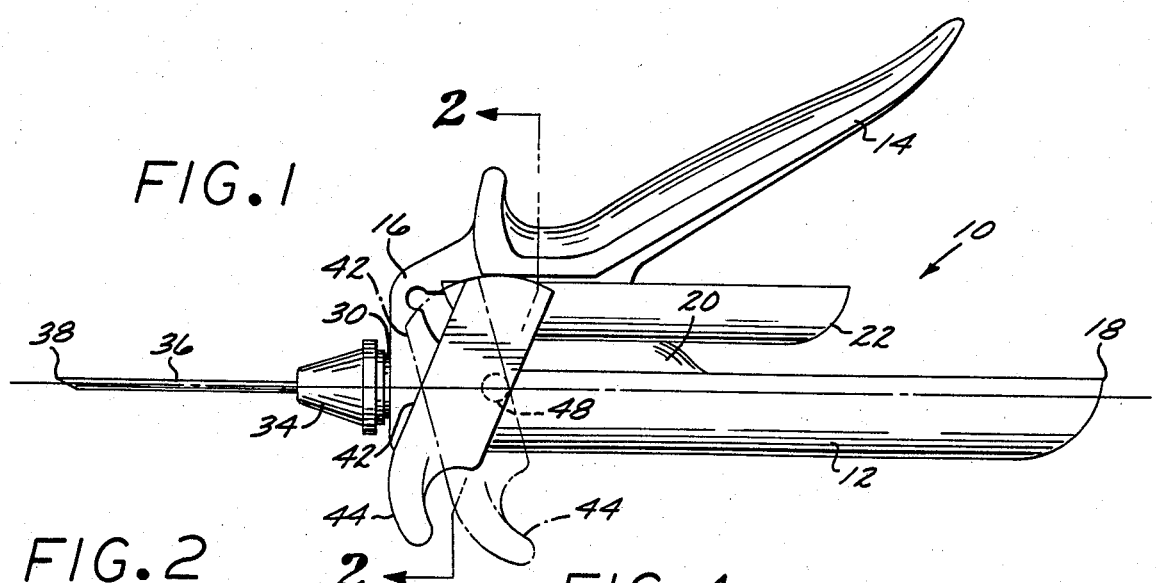
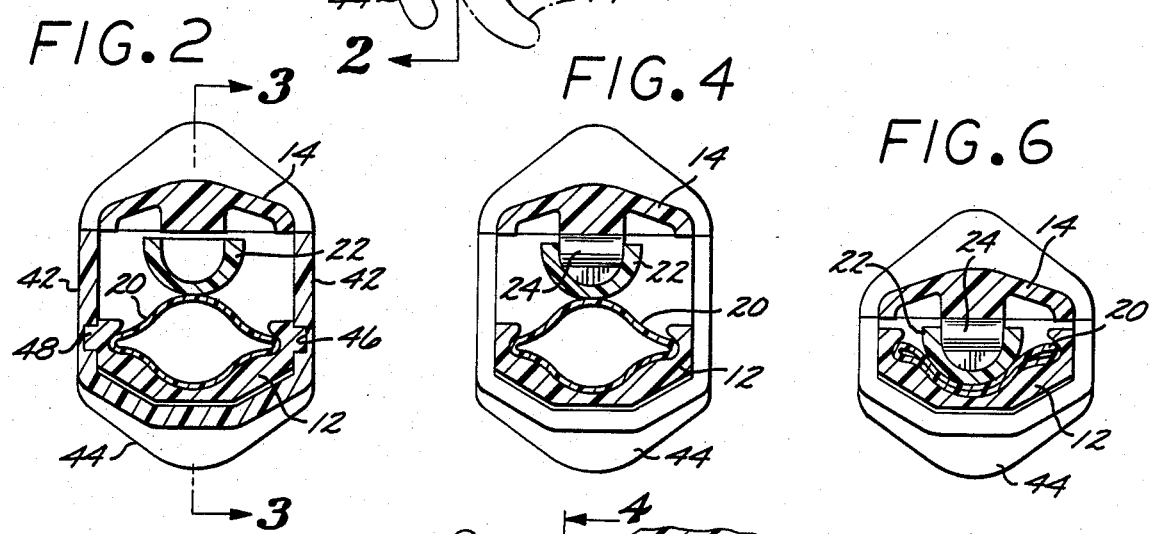
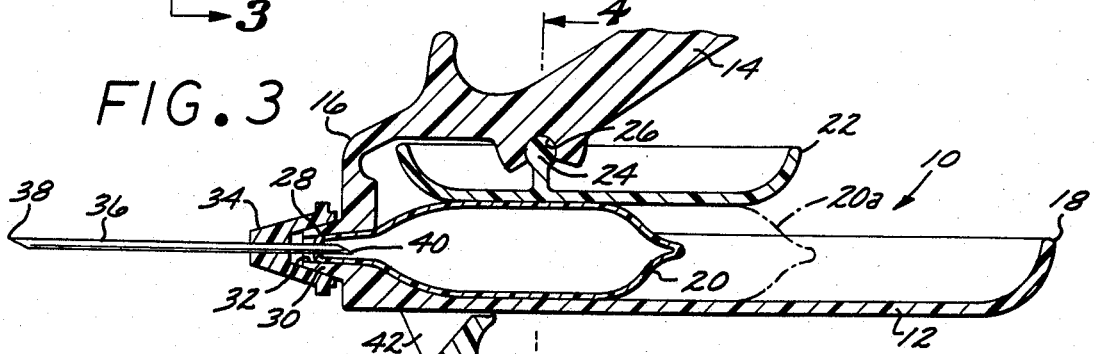
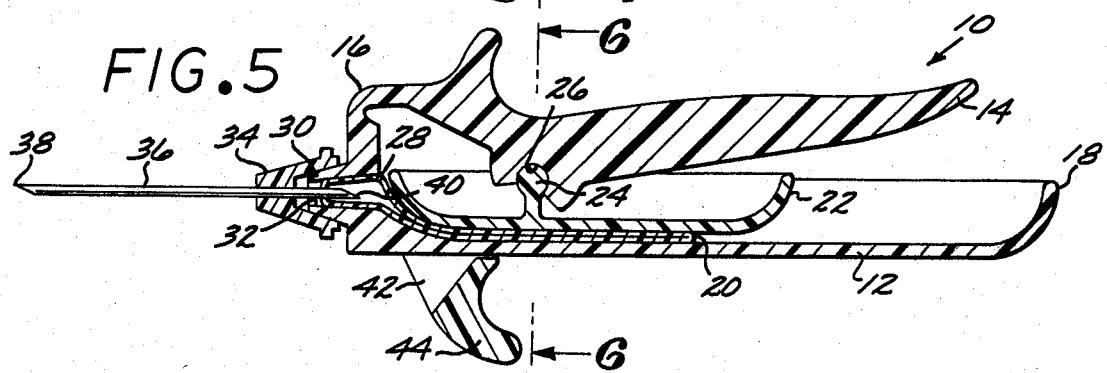

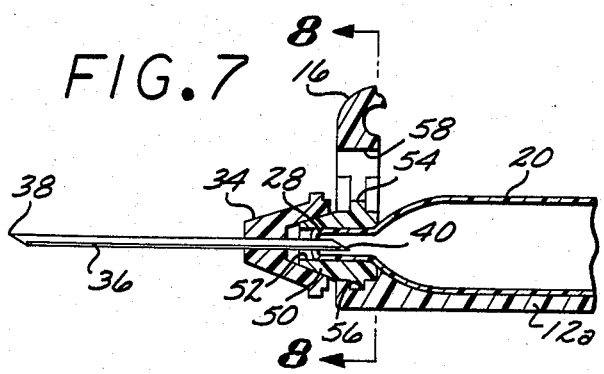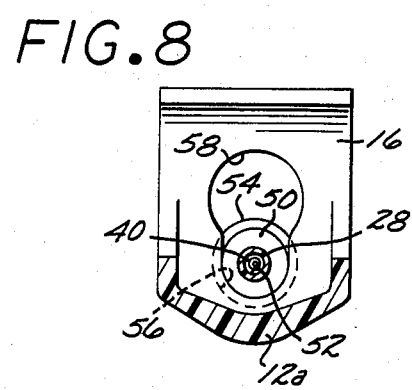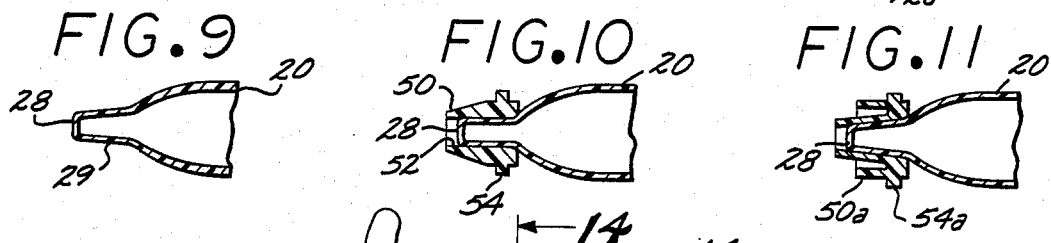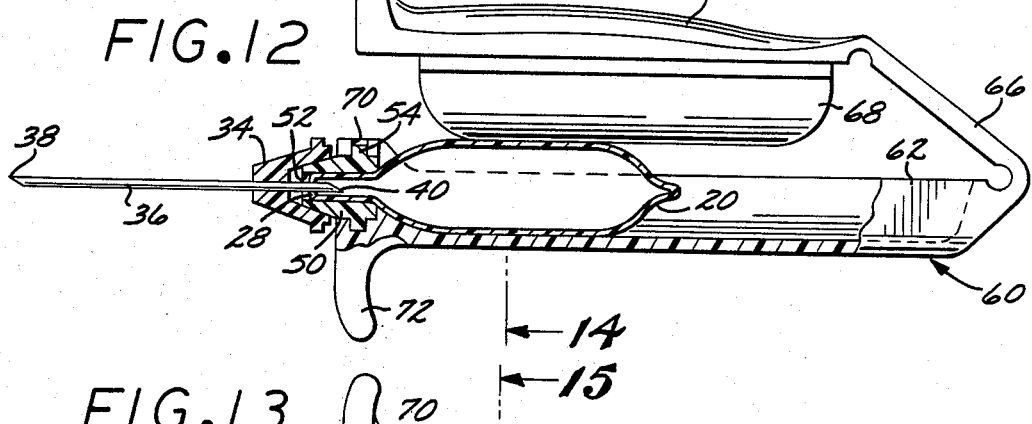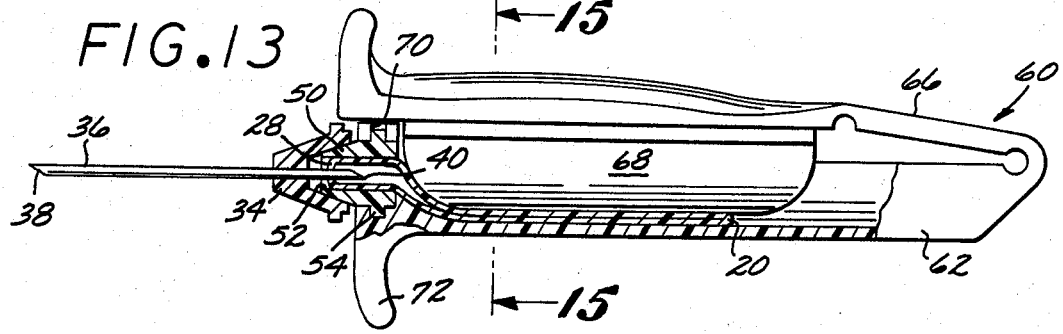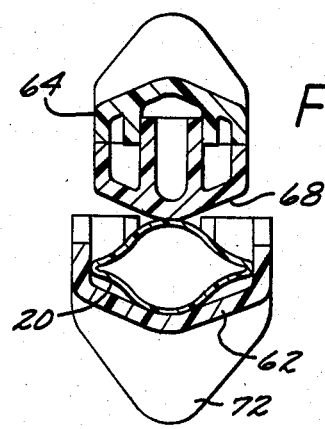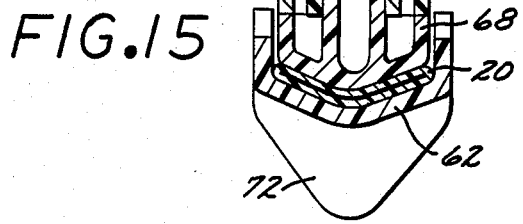

SQUEEZE-ACTUATED SYRINGE

BACKGROUND OF THE INVENTION

This invention relates generally to the field of syringes for injecting a medicinal liquid into a patient (human or animal) via a hypodermic needle. In particular, it relates to a syringe adapted for use with a disposable needle and a self-contained, disposable reservoir or ampoule of medicinal liquid, wherein the liquid is discharged from the ampoule by compressing or squeezing the ampoule.

Conventional hypodermic syringes comprise a tubular reservoir with a fitting at one end for the attachment of a hypodermic needle. The other end of the reservoir is provided with a plunger. Syringes of this type must be filled from a separate vial or ampoule in the well known manner of pushing the plunger all the way into the reservoir, inserting the needle into the vial, and pulling the plunger out until the reservoir is filled to the desired level, as indicted by volumetric markings on the reservoir wall. Before injection, a small amount of liquid must be expressed through the needle to assure that no air is injected. This is especially important with intravenous injections, where injected air could cause a fatal embolism.

Several disadvantages of these conventional syringes have been recognized. For example, the need to fill the syringe from a separate vial is cumbersome and time-consuming, as is the need precisely to measure the dosage and then express the liquid to remove air from the syringe. Also, the plunger mechanism can be awkward to manipulate in certain situations, and, in any case, requires at least some degree of dexterity. This can present a problem in certain applications, such as in the application of local anesthesia, where an injection must be made into a relatively inaccessible part of the body. Patients, such as diabetics, who must perform self-injections, and particularly those who are elderly, weak, or infirm, sometimes find it difficult to inject themselves with the plunger-type syringe.

Accordingly, attempts have been made to provide alternative syringe designs which overcome the disadvantages of the plunger mechanism. One approach has been to provide a syringe with a self-contained reservoir or ampoule pre-filled with a precisely measured amount of medicament. The ampoule has flexible walls, so that its contents can be discharged by compressing or squeezing it. Devices of this type are exemplified in the following U.S. patents:

| U.S. Pat. No. | Patentee |
| --- | --- |
| 798,093 | Dean |
| 2,618,263 | Lakso, et al. |
| 3,099,264 | Hubbard |
| 3,114,369 | Hall |
| 4,013,073 | Cunningham |
| 4,475,906 | Holzner |

While the above-listed prior art devices do, in varying degrees, avoid the aforementioned problems associated with the plunger-type syringe, none has found widespread acceptance by medical practitioners, for a variety of reasons. For example, some of the prior art devices offer insufficient physical support for the needle during injection, making their use awkward at best. Others require a degree of dexterity in their use that, while possibly an improvement over the plunger-type syringe, still renders them ill-suited for self-injection, especially by the physically feeble. Another drawback in some prior art devices is their inability to be used with disposable needles. In such devices, the syringe and needle are manufactured as a disposable unit, a practice some may consider wasteful. Also, in devices of this type, some mechanism must be included to prevent the flow of liquid from the reservoir into the needle until an injection is to be performed. Such a mechanism adds to the complexity, and thus the cost, of such devices.

There has thus been a long-felt, but not entirely satisfied, need for a syringe that contains a pre-measured reservoir or ampoule of medicament, which provides good physical support for the needle and which offers an injection mechanism that is easy to manipulate without much dexterity or strength. The need has also been felt for a syringe of this nature which can use disposable needles, and which, therefore, does not require means for blocking the flow from the reservoir into a pre-attached needle.

SUMMARY OF THE INVENTION

Broadly, the present invention is a squeeze-actuated syringe including a rigid body that provides both a stationary grip and an open receptacle for a collapsible ampoule containing a liquid to be injected. A handle is attached by a hinge to one end of the body and carries a compression pad in opposed relationship to the ampoule disposed in the receptacle. The handle and the body are configured to be gripped in a person's hand, and the handle squeezed toward the receptacle to bring the pad to bear against the ampoule. The body has a fitting at its proximal end which is adapted for the attachment of a removable needle (such as a disposable hypodermic needle). When the needle is attached to the fitting, the inner or distal end of the needle passes through the fitting and punctures the ampoule, allowing the contents of the ampoule to be discharged through the needle as the ampoule is compressed by the pressures applied through the squeezing of the pad against it.

More specifically, in a preferred embodiment, the handle is attached by a hinge to the proximal end of the body. The pad is attached to the underside of the handle by a pivoting joint which allows the pad to remain aligned substantially parallel with the longitudinal axis of the body as the handle is squeezed. In an alternative embodiment, the handle is attached by a hinge to the distal end of the body. The hinge in this alternative embodiment is itself configured to maintain the parallel alignment between the longitudinal axes of the pad and the body.

In both embodiments, a locking mechanism may advantageously be employed to lock the handle in its fully extended ("unsqueezed") position, to prevent accidental or inadvertent injection. This locking mechanism may take the form of a lever pivotally attached to the body and capable of being selectively moved into and out of engagement with the handle.

The ampoule employed with the syringe is a collapsible sack of resilient material filled with a pre-measured amount of liquid medicament. The proximal end of the ampoule is formed into a rupturable nipple which is enclosed, at least partially, by a central internal passage in the fitting. When a needle is attached to the fitting, as previously mentioned, the distal end of the needle enters the passage through an external opening and punctures the nipple. The fitting may be made integral with the body, with the ampoule being either separately removable from, or disposable with, the syringe assembly. Alternatively, the fitting may be removable from the body as a unit with the ampoule, the remainder of the syringe (body and handle) being re-usable. It is felt to be preferred to have the body and handle re-usable regardless of the configuration of the needle attachment fitting.

The present invention offers significant advantages over prior art syringes. Of key importance is the squeeze action by which the injection is performed. The mechanism which squeezes the ampoule to discharge its contents requires little strength or dexterity for actuation, making it highly advantageous for use by weak or infirm patients who must inject themselves with medication. This feature is also advantageous for injections that must be made into relatively inaccessible parts of the body.

Another advantageous feature of the invention is its use of pre-filled ampoules containing pre-measured doses of medication. This eliminates the need to fill the syringe reservoir from a separate vial before injection, thereby not only saving time, but also providing a more accurately measured dosage. The action of the pad in compressing the ampoule also provides a uniform flow through the needle with considerably less conscious effort than is required with the plunger-type syringe.

By using removable (i.e., disposable) needles, the present invention offers the convenience and economy associated with such needles. Moreover, because the ampoule remains sealed until the needle is attached, there is no need for any separate mechanism (e.g., a valve or a plunger) to prevent inadvertent flow from the ampoule into the needle. (The locking mechanism optionally employed with the present invention minimizes the risk of such inadvertent flow even *after* the needle is attached.)

Another advantage enjoyed by the present invention is that it can accommodate, in a single syringe body, ampoules of widely varying volumetric capacities, and even large volumes can be injected with good flow rate uniformity, with substantially less physical effort than is required with plunger-type syringes. Enhancing the ability to provide low-effort injection with good flow control is the rigid support for the needle provided by the body and the needle attachment fitting.

As will be best appreciated from the detailed description which follows, these and other advantages which will be made apparent overcome the aforementioned problems associated with prior art syringes, and provide a significant advancement in the state of the art.

BRIEF DESCRIPTION OF THE DRAWINGS

FIG. 1 is a side elevational view of a first preferred embodiment of the invention;

FIG. 2 is a cross-sectional view taken along line 2—2 of FIG. 1, showing the handle of the syringe in its locked position;

FIG. 3 is a cross-sectional view taken along line 3—3 of FIG. 2, showing the handle unlocked, but in its position before injection;

FIG. 4 is a cross-sectional view taken along line 4—4 of FIG. 3;

FIG. 5 is a cross-sectional view similar to FIG. 4, but showing the syringe after an injection has been made;

FIG. 6 is a cross-sectional view taken along line 6—6 of FIG. 5;

FIG. 7 is a partial cross-sectional view taken along the longitudinal axis of the syringe, showing a variation of the needle attachment fitting;

FIG. 8 is a cross-sectional view taken along line 8—8 of FIG. 7;

FIGS. 9, 10, and 11 are partial cross-sectional views of the ampoule used in the present invention, FIG. 10 showing the ampuole with the fitting of FIGS. 7 and 8, and FIG. 11 showing an alternative fitting;

FIG. 12 is a side elevational view, partially in longitudinal cross-section, of a second preferred embodiment of the present invention, showing the elements of the invention in their pre-injection configurations;

FIG. 13 is a view similar to that of FIG. 12, showing the elements of the invention in their post-injection configurations;

FIG. 14 is a cross-sectional view taken along line 14—14 of FIG. 12; and

FIG. 15 is a cross-sectional view taken along line 15—15 of FIG. 13.

DETAILED DESCRIPTION OF THE INVENTION

Referring now to the drawings, a syringe assembly 10 in accordance with a first preferred embodiment of the invention is shown in FIGS. 1 through 6. The syringe assembly 10 comprises a rigid, elongate body 12 having a proximal end to which a handle 14 is attached by a hinge 16, and a distal end 18 opposite the proximal end. The sides of the body curve upwardly and define a generally concave interior surface which, as will be described below, preferably has a contour generally conforming to the external surface of a collapsible ampoule 20 which is disposed on the interior surface. Thus, the interior surface of the body 12 forms an open receptacle for the ampoule 20.

In this preferred embodiment, the handle 14 is hinged at its proximal end to the proximal end of the body 12. The distal end of the handle is, in its "open" (pre-injection) position, angled upwardly away from the body, as shown in FIG. 1. Carried on the underside of the handle 14, closer to the proximal end than to the distal end thereof, is a pad 22, which is thus disposed, with the handle 14, in opposed relationship to the receptacle formed by the interior surface of the body 12. The pad 22 is attached to the handle by a cylindrical pivot 24 which is received in a socket 26 on the underside of the handle 14. The purpose of this arrangement will shortly be made apparent.

The collapsible ampoule 20 used in the present invention is a hollow sack of a resilient material, such as a suitable plastic. It is pre-filled with a pre-measured volume of a liquid, such as a medicament, and sealed. Although the ampoule 20 can be made in a variety of specific configurations, preferably it has a somewhat flattened perimeter, so that it is thicker in the middle than at the edges. As shown in detail in FIG. 9, the proximal end of the ampoule 20 is formed into a projection or nipple 28 which may have somewhat thinner walls 29 than the remainder of the ampoule 20, so that it may be more easily ruptured. Ampoules of widely varying sizes (volumetric capacities) can be accommodated in the body 12, as shown in broken outline 20a (FIG. 3).

As best shown in FIGS. 3 and 5, the proximal end of the body 12 terminates in a needle attachment fitting 30, shown in this variant of the invention to be formed integrally with the rest of the body, and with the hinge 16. The fitting 30 has a central axial passage 32 into which extends the nipple 28 so as to be at least substantially enclosed within the fitting 30. The exterior surface of the fitting 30 is tapered to mate with a female fitting 34 on a needle 36. The needle 36 is a double-ended needle, extending both proximally and distally from the fitting 34. It has a sharply pointed proximal end 38 and, advantageously, a pointed distal end 40. With the exception of the distal extension beyond the fitting 34, the needle 36 is similar to disposable hypodermic needles of conventional design. When the needle is attached to the syringe by the mating of the fittings 30 and 34, the distal end 40 enters the axial passage 32 through an external opening and punctures or ruptures the nipple 28, thereby allowing the contents of the ampoule 20 to flow into the needle 36, as will be described below.

The embodiment of FIGS. 1 through 6 is shown with a locking mechanism which, although optional, is highly advantageous. The locking mechanism comprises a pair of generally parallel lever arms 42 disposed on either side of the body 12 and joined together at the bottom (underneath the body 12) to form a tang 44 adapted for engagement by a person's finger. Each of the lever arms 42 has a socket 46 which receives a projection or pin 48 extending from either side of the body 12 (FIG. 2). The sockets 46 and pins 48 form a pivot for the lever arms, so that they can be moved between a first position (solid outline in FIG. 1) and a second position (broken outline in FIG. 1). In the first position, the handle 14 is engaged by the ends of the lever arms 42 opposite the tang 44, and the handle is thereby locked in a fixed position relative to the body 12, this position being the "open" or "pre-injection" position, in which the pad 22 is not pressed against the ampoule 20. When the tang 44 is pulled forward, the lever arms are moved to the second position, out of engagement with the handle, thereby allowing the handle to be squeezed to compress the ampoule, as will be described below.

The operation of the preferred embodiment of FIGS. 1 through 6 will now be easily understood. With the locking lever arms 42 in their locked position, an ampoule 20 is placed in the body 12 with its nipple 28 inserted into the passage 32. A disposable needle 36 is attached to the body by way of the fittings 30 and 34, as described above, so that the distal end 40 of the needle punctures the nipple 28. When the injection is to be made, the locking levers 42 are pulled to the unlocked position. The syringe is gripped in one hand, the exterior surface of the body 12 acting as a stationary grip. The handle 14 is squeezed toward the body, thereby applying pressure to the ampoule 20 via the pad 22. The ampoule 22 is thereby compressed, discharging its contents through the needle 36.

Uniform flow from the ampoule 20, and a substantially complete emptying of its contents, are aided by two features of the invention. Specifically, the interior surface of the body 12 has, as previously mentioned, a contour conforming generally to the shape of the ampoule 20. This feature allows a substantially complete collapsing of the ampoule 20 by the pad 22, as shown in FIG. 6, thereby providing for a near total emptying of the ampoule's contents (except for an insignificant volume remaining in the nipple). The contour of the interior body surface also keeps the ampoule securely in place during the injection, further aiding the uniformity of flow and the totality of discharge.

The pivot 24 and socket 26 allow the longitudinal axis of the pad 22 to remain aligned substantially parallel to the longitudinal axis of the body 12 as the handle 14 is squeezed, as shown in FIGS. 3 and 5. This feature also enhances the ability of this syringe to discharge substantially the entire contents of the ampoule at a uniform rate of flow.

FIGS. 7, 8, and 10 illustrate a variation of the first preferred embodiment of FIGS. 1 through 6, in which a removable needle attachment fitting 50 is employed, in place of the integral fitting 30. The removable fitting 50 is advantageously provided pre-attached to the ampoule 20, the nipple 28 of the ampoule being secured within an axial passage 52 in the fitting. The fitting 50 has an annular flange 54, and the fitting, with the ampoule attached, is installed in the syringe body 12 by seating the flange 54 in a slot 56, access to which is provided by an oversized aperture 58 between the syringe body 12a and the hinge 16.

FIG. 11 shows a modified removable fitting 50a which is specifically adapted as a luer connection fitting. This modified fitting may be of utility when the syringe is employed to inject a liquid into a catheter, cannula, or tube provided with a mating luer fitting. The fitting 50a has a flange 54a which is seated in the slot 56 at the proximal end of the body 12a, in the manner described above.

FIGS. 12 through 15 show a second preferred embodiment 60 of the invention. This embodiment differs from the previously-described embodiment principally in its having a movable handle which is attached to the distal end of the body, rather than to the proximal end.

Specifically, this second embodiment has a body 62 which has a generally convex exterior gripping surface, and a generally concave internal surface forming a receptacle for an ampoule 20, of the type previously described. The body 62 extends longitudinally between a proximal end and a distal end with a movable handle 64 attached by a hinge 66 to the distal end. A pad 68 is attached to the underside of the handle 64 in opposed relationship to the receptacle formed by the interior surface of the body 62. The hinge 66 is double-jointed, allowing the handle 64 to move slightly toward the proximal end of the syringe as it is squeezed toward the body 62, and also allowing the longitudinal axis of the pad 68 to remain aligned substantially parallel to the longitudinal axis of the body as the handle is squeezed.

The proximal end of the body 62 has a slot 70, into which can be inserted the flange 54 of the removable fitting 50 described above, for the installation of an ampoule/fitting assembly of the type shown in FIGS. 7 and 10, or, alternatively, of the type shown in FIG. 11. As an alternative, the needle attachment fitting may be formed integrally with the body, in a manner similar to that shown in FIGS. 3 and 5. If such an alternative construction is employed, of course, only the ampoule 20 itself is removable. Nevertheless, because the slot 70 is easily provided at the proximal end of the body 62 to accommodate the flange 54 of the removable fitting 50, the use of the removable fitting 50 is preferred with this embodiment.

Extending from the proximal end of the body 62 opposite the slot 70 is a tang 72 formed integrally with the body. The tang 72 provides a finger stop or rest when the syringe is gripped in one's hand. Alternatively, the tang 72 can be made part of a locking mechanism, of the type described above with respect to the embodiment of FIGS. 1 through 6.

The operation of this second embodiment is similar to that of the first embodiment. With an ampoule 20 placed in the body, a needle 36 with its attached female fitting 34 is fixed to the male attachment fitting 50 of the syringe, the distal end 40 of the needle thereby entering the passage 52 in the male attachment fitting 50 and puncturing the ampoule nipple 28. The handle 64 and the body 62 are gripped in one hand, and the handle is squeezed toward the body, thereby compressing the ampoule to discharge its contents into the needle. The double jointed hinge 66, as previously mentioned, causes the handle 64 to move forwardly (toward the proximal end of the body) as it moves downwardly toward the body, while maintaining the longitudinal axes of the body and the pad 68 substantially parallel. This action provides both uniformity of flow and a substantially complete emptying of the ampoule, much as the pivoting action of the pad 22 in the previously described embodiment of FIGS. 1 through 6.

When the injection is completed, the empty ampoule 20 is removed, either with the removable fitting 50, or by itself, if the integral fitting 30 is used.

It can be appreciated from the foregoing that the present invention, in either of the embodiments described above, offers a number of significant advantages. Most obviously, the use of a squeeze-action mechanism to effect the injection makes the syringe easier to manipulate and more convenient to use than the conventional plunger-type syringe. This feature facilitates self-injection for patients who lack the strength or dexterity to actuate or manipulate a plunger-type syringe in a controlled manner. Also, injection into relatively inaccessible body areas is made easier.

The ease of use of the present invention is further enhanced by its employment of pre-measured ampoules, thereby obviating the need to fill the syringe from a separate vial. Another feature contributing to ease of use is that, unlike the many prior art squeeze-actuated syringes, the present invention provides rigid support (via the syringe body 12, 12a, or 62) for the needle. In addition, uniform flow is controllably maintained with the squeeze-action mechanism, even near the end of the injection, and, unlike some prior art syringes which employ pre-filled ampoules, substantially total emptying of the ampoule can be controllably effected with ease. Moreover, ampoules of varying volumetric capacities can be accommodated, and the injection of large volumes (e.g., greater than 10 cc) of medicament can be effected much more easily than with plunger-type syringes.

In addition to these advantages is ease and convenience of use, the present invent offers further advantages in terms of cost. For example, the use of disposable needles and disposable ampoules minimizes the need for costly cleaning and sterilizing procedures. This advantage is further enhanced if the removable needle attachment fitting is employed. In addition, the use of disposable needles further contributes to the cost savings by obviating the need for a mechanism to prevent a pre-attached needle from rupturing the ampoule.

While two embodiments, and several modifications of these embodiments have been described herein, it should be noted that still further modifications will suggest themselves to those skilled in the pertinent arts. For example, the body and the ampoule can assume a number of configurations, as can the handle hinging mechanism and the means for removably attaching the removable needle attachment fitting to the syringe body. Similarly, the locking mechanism described herein is exemplary only, and different, but functionally equivalent, locking mechanisms may be devised. These and other modifications should be considered within the spirit and scope of the present invention, as defined in the claims which follow.

What is claimed is:

1. A syringe assembly, comprising:
    an elongate body having an exterior surface forming a stationary grip member and an interior surface defining an open receptacle adapted to receive a collapsible, liquid-filled ampoule, said exterior and interior surfaces each extending from a proximal end to a distal end;
    connection means at said proximal end of said body for allowing the attachment of a removable needle to said body, whereby said needle, when attached to said body by said connection means, has a distal end which punctures said ampoule;
    a handle disposed in opposed relationship to said open receptacle and forming a movable grip member, said handle having an end attached by hinge means to one of said proximal and distal ends of said body, whereby said handle can be moved toward said ampoule disposed in said receptacle when said stationary and movable grip members are gripped in a person's hand;
    pressure application means on said handle for applying pressure to said ampoule to discharge the liquid therefrom when said handle is moved toward said ampoule; and
    parallel alignment means, operatively associated with said handle, for maintaining said pressure application means in substantially parallel alignment with the longitudinal axis of said body as said handle is moved toward said body.

2. The syringe assembly of claim 1, wherein said handle has a proximal end attached by said hinge means to said proximal end of said body, and said parallel alignment means includes a pivotal attachment between said pressure application means and said handle.

3. The syringe assembly of claim 1, wherein said handle has a distal end attached by said hinge means to said distal end of said body, and said hinge means is a double-jointed hinge that provides said parallel alignment means.

4. The syringe assembly of claim 1, further comprising:
    locking means, engageable between said body and said handle, for selectively locking said handle in a fixed position relative to said body.

5. The syringe assembly of claim 4, wherein said locking means comprises:
    a lever having a first end adapted and positioned to be engageable by a person's finger and a second end engageable against said handle near said proximal end thereof; and
    pivot mean for pivotally attaching said lever between said first and second ends to said body at a pivot point located closer to said proximal end thereof than to said distal end thereof;
    whereby said lever is pivotable about said pivot point between a first position in locking engagement against said handle, and a second position disengaged from said handle.

6. The syringe assembly of claim 1, wherein said ampoule has a proximal end with a rupturable portion, and wherein said connection means comprises:

a fitting having an interior passage enclosing said rupturable portion, and an exterior surface adapted for the attachment of said removable needle;

whereby said passage has an external opening that allows the entry of the distal end of said needle to rupture said rupturable portion of said ampoule when said needle is attached to said exterior surface of said fitting.

7. The syringe assembly of claim 6, wherein said fitting is integral with said body, and wherein said ampoule is removable from said fitting and from said receptacle.

8. The syringe assembly of claim 6, wherein said fitting is removable from said body, and wherein said ampoule is removable with said fitting.

9. A syringe for discharging a liquid from a collapsible ampoule through a hypodermic needle or the like, comprising:

body means having an exterior surface forming a stationary grip member and an interior surface defining a receptacle for said ampoule, said interior and exterior surfaces each extending from a proximal end to a distal end;

handle means disposed in opposed relationship to said interior surface of said body means and forming a movable grip member;

hinge means for attaching said handle means to one of said proximal and distal ends of said body means to allow said handle means to be moved toward said interior surface of said body means when said body means and said handle means are gripped in a person's hand;

pressure application means on said handle means for applying pressure to an ampoule disposed in said body means when said handle means is moved toward said body means;

parallel alignment means, operatively associated with said handle means, for maintaining said pressure application means in substantially parallel alignment with the longitudinal axis of said body means as said handle means is moved toward said body means; and connection means at said proximal end of said body means for allowing the attachment of a removable needle to said body means, said needle having a proximal end and a distal end, whereby the attachment of said needle causes the distal end of said needle to puncture said ampoule when said ampoule is disposed in said body means.

10. The syringe of claim 1, wherein said hinge means attaches said handle means to said proximal end of said body means.

11. The syringe of claim 1, wherein said hinge means attaches said handle means to said distal end of said body means.

12. The syringe of claim 1, further comprising:

locking means, engageable between said body means and said handle means, for selectively locking said handle means in a fixed position relative to said body means.

13. The syringe of claim 12, wherein said locking means comprises:

a lever having a first end adapted and positioned to be engaged by a person's finger and a second end engageable against said handle means; and pivot means for pivotally attaching said lever between said first and second ends to said body means distally from said proximal end thereof;

whereby said lever is pivotable between a first position in locking engagement against said handle means, and a second position disengaged from said handle means.

14. The syringe of claim 10, wherein said parallel alignment means comprises a pivotal attachment between said pressure application means and said handle means.

15. The syringe of claim 1, wherein said syringe is adapted for use with an ampoule that includes a first fitting for the attachment of said needle, and wherein said connection means includes a second fitting at said proximal end of said body means with which said first fitting is removably co-engageable.

16. The syringe of claim 11, wherein said hinge means is a double-jointed hinge which provides said parallel alignment means.

17. A syringe assembly, comprising:

a body having a proximal end and a distal end with a concave surface extending therebetween;

a collapsible ampoule filled with a pre-measured volume of liquid disposed on said concave surface, said ampoule having a proximal end with a rupturable portion;

squeeze-actuated means, operably connected to said distal end of said body, for applying pressure against said ampoule when said squeeze-actuated means is squeezed toward said concave surface with said ampoule disposed thereon, said squeeze-actuated means comprising a handle disposed in opposed relationship to said concave surface, and having a distal end connected by double-jointed hinge means to said distal end of said body, whereby said handle is maintained in substantially parallel alignment with the longitudinal axis of said body as said handle is squeezed toward said concave surface; and connection means at said proximal end of said body, said connection means including an interior passage enclosing a substantial part of said rupturable portion of said ampoule and an exterior surface adapted for the attachment of a removable needle having a proximal end and a distal end, whereby said passage has an external opening that allows the entry of the distal end of said needle to rupture said rupturable portion of said ampoule when said needle is attached to said exterior surface of said connection means, and whereby the contents of said ampoule is discharged through said rupturable portion and said fitting into said needle by the compression of said ampoule under the application of said pressure.

18. The syringe assembly of claim 17, further comprising:

locking means, engageable between said body and said handle, for selectively locking said handle in a fixed position relative to said body.

19. The syringe assembly of claim 17, wherein said connection means is integral with said body, and wherein said ampoule is removable from said fitting and from said concave surface.

20. The syringe assembly of claim 17, wherein said connection means is removable from said body, and wherein said ampoule is removable with said connection means.

21. A syringe assembly, comprising:

a body having a proximal end and a distal end with a concave surface extending therebetween;

a collapsible ampoule filled with a pre-measured volume of liquid disposed on said concave surface, said ampoule having a proximal end with a rupturable portion;

a handle disposed in opposed relationship to said concave surface, and having a proximal end and a distal end;

hinge means, connecting said proximal end of said handle to said proximal end of said body, whereby said handle is pivoted on said hinge means when said handle is squeezed toward said concave surface;

a pad operable with said handle so as to be engageable against said ampoule to apply pressure thereto when said handle is squeezed toward said concave surface;

means for pivotally attaching said pad to said handle so that said pad remains in substantially parallel alignment with the longitudinal axis of said body as said handle is squeezed toward said concave surface; and connection means at said proximal end of said body, said connection means including an interior passage enclosing a substantial part of said rupturable portion of said ampoule and an exterior surface adapted for the attachment of a removable needle having a proximal end and a distal end, whereby said passage has an external opening that allows the entry of the distal end of said needle to rupture said rupturable portion of said ampoule when said needle is attached to said exterior surface of said connection means, and whereby the contents of said ampoule is discharged through said rupturable portion and said fitting into said needle by the compression of said ampoule under the application of said pressure.

22. The syringe assembly of claim 21, further comprising:

locking means, engageable between said body and said handle, for selectively locking said handle in a fixed position relative to said body.

23. The syringe assembly of claim 21, wherein said connection means is integral with said body, and wherein said ampoule is removable from said fitting and from said concave surface.

24. The syringe assembly of claim 21, wherein said connection means is removable from said body, and wherein said ampoule is removable with said connection means.

25. A syringe for discharging a liquid from a collapsible ampoule through a hypodermic needle or the like, comprising:

body means having an exterior surface forming a stationary grip member and an interior surface defining a receptacle for said ampoule, said interior and exterior surfaces each extending from a proximal end to a distal end;

handle means disposed in opposed relationship to said interior surface of said body means and forming a movable grip member;

hinge means for attaching said handle means to one of said proximal and distal ends of said body means to allow said handle means to be moved toward said interior surface of said body means when said body means and said handle means are gripped in a person's hand;

pressure application means on said handle means for applying pressure to an ampoule disposed in said body means when said handle means is moved toward said body means;

connection means at said proximal end of said body means for allowing the attachment of a removable needle to said body means, said needle having a proximal end and a distal end, whereby the attachment of said needle causes the distal end of said needle to puncture said ampoule when said ampoule is disposed in said body means; and locking means, engageable between said body means and said handle means, for selectively locking said handle means in a fixed position relative to said body means, said locking means comprising:

a lower having a first end adapted and positioned to be engaged by a person's finger and a second end engageable against said handle means; and pivot means for pivotally attaching said lever between said first and second ends to said body means distally from said proximal end thereof;

whereby said lever is pivotable between a first position in locking engagement against said handle means, and a second position disengaged from said handle means.

26. A syringe assembly, comprising:

an elongate body having an exterior surface forming a stationary grip member and an interior surface defining an open receptacle adapted to receive a collapsible, liquid-filled ampoule, said exterior and interior surfaces each extending from a proximal end to a distal end;

connection means at said proximal end of said body for allowing the attachment of a removable needle to said body, whereby said needle, when attached to said body by said connection means, has a distal end which punctures said ampoule;

a handle disposed in opposed relationship to said open receptacle and forming a movable grip member, said handle having an end attached by hinge means to one of said proximal and distal ends of said body, whereby said handle can be moved toward said ampoule disposed in said receptacle when said stationary and movable grip members are gripped in a person's hand;

pressure application means on said handle for applying pressure to said ampoule to discharge the liquid therefrom when said handle is moved toward said ampoule; and locking means, engageable between said body and said handle, for selectively locking said handle in a fixed position relative to said body, said locking means comprising:

a lever having a first end adapted and positioned to be engageable by a person's finger and a second end engageable against said handle near said proximal end thereof; and pivot means for pivotally attaching said lever between said first and second ends to said body at a pivot point located closer to said proximal end thereof than to said distal end thereof;

whereby said lever is pivotable about said pivot point between a first position in locking engagement against said handle, and a second position disengaged from said handle.

* * * * *

UNITED STATES PATENT AND TRADEMARK OFFICE
CERTIFICATE OF CORRECTION

PATENT NO. : 4,581,021
DATED : April 8, 1986
INVENTOR(S) : Boris Landau and Marius Saines It is certified that error appears in the above-identified patent and that said Letters Patent are hereby corrected as shown below:

```
Column 5, line 54, change "ampoule 22" to --ampoule 20--.

Column 9, line 50, change "claim 1" to --claim 9--;
          line 53, change "claim 1" to --claim 9--;
          line 56, change "claim 1" to --claim 9--.

Column 10, line 9, change "claim 1" to --claim 9--.

Column 12, line 16, change "lower" to --lever--.
```

Signed and Sealed this

Fifteenth Day of July 1986

[SEAL]

Attest:

Attesting Officer

DONALD J. QUIGG

Commissioner of Patents and Trademarks